United States Patent
Wall et al.

[11] Patent Number: 5,322,110
[45] Date of Patent: Jun. 21, 1994

[54] DENTAL PROSTHETIC JOINING PROCESS BY CASTING-ON AND PRIMARY MOULDS THEREFOR

[75] Inventor: Giselher Wall, Ludwigstr., D-8730 Bad Kissingen; Manfred Lutzmann, Garbsen, both of Germany

[73] Assignee: Giselher Wall, Bad Kissingen, Fed. Rep. of Germany

[21] Appl. No.: 773,589

[22] PCT Filed: May 17, 1990

[86] PCT No.: PCT/DE90/00370

§ 371 Date: Jan. 17, 1992

§ 102(e) Date: Jan. 17, 1992

[87] PCT Pub. No.: WO90/14053

PCT Pub. Date: Nov. 29, 1990

[30] Foreign Application Priority Data

May 20, 1989 [DE] Fed. Rep. of Germany ....... 3916562

[51] Int. Cl.5 .................. B22D 19/00; A61C 13/08
[52] U.S. Cl. .................... 164/100; 164/98; 164/DIG. 4; 433/183; 433/208; 433/224
[58] Field of Search ............. 164/98, 100, 101, 111, 164/DIG. 4; 433/180, 181, 183, 206, 207, 208, 224

[56] References Cited

U.S. PATENT DOCUMENTS

| 3,337,956 | 8/1967 | Lirot | 164/111 |
| 4,450,886 | 5/1984 | Enomoto | 164/100 |
| 4,494,287 | 1/1985 | Cruzen | 164/101 |
| 4,895,516 | 1/1990 | Hulten | 433/208 |

FOREIGN PATENT DOCUMENTS

| 3622511 | 1/1988 | Fed. Rep. of Germany . | |
| 54-160520 | 12/1979 | Japan | 164/100 |
| 58-44949 | 3/1983 | Japan | 164/100 |
| 59-174262 | 10/1984 | Japan | 164/100 |
| 62-173065 | 7/1987 | Japan | 164/100 |
| 1131594 | 12/1984 | U.S.S.R. | 164/100 |

*Primary Examiner*—Paula A. Bradley
*Assistant Examiner*—Rex E. Pelto
*Attorney, Agent, or Firm*—Cushman, Darby & Cushman

[57] ABSTRACT

In a dental prosthetic casting-on process, in which a secondary part made of metal is cast-on to a primary part made of metal, a primary part made from an oxide-forming metal alloy may be used if the latter's casting-on surface is alloyed, prior to casting-on, with a reducing metalloid. In this regard, boron, silicon or phosphorus, for example, can be made to diffuse into the surface lattice of the primary part. A primary part made from an oxide-forming dental alloy and suitable for such a casting-on process exhibits in its casting-on surface an enhanced boron or silicon or phosphorus content.

6 Claims, 2 Drawing Sheets

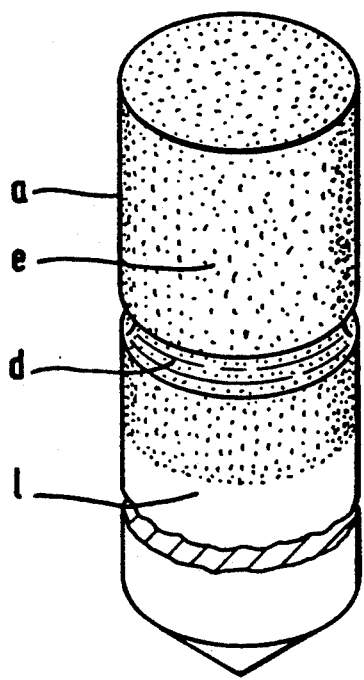 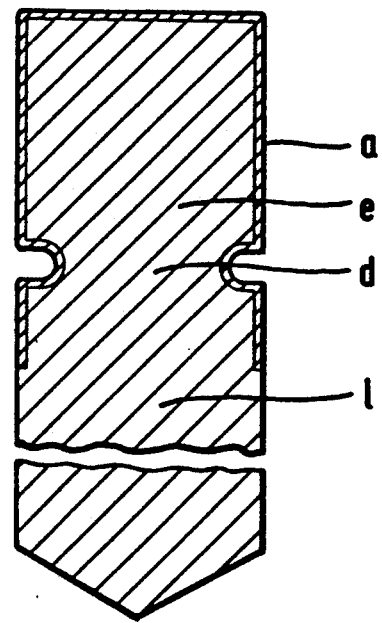
Fig.3a　　　　　　　　Fig.3b
Fig.3

DENTAL PROSTHETIC JOINING PROCESS BY CASTING-ON AND PRIMARY MOULDS THEREFOR

BACKGROUND OF THE INVENTION

1. Field of the Invention

The invention relates to a dental prosthetic casting-on process and to a dental prosthetic primary part, which is suitable for the casting-on process.

2. Description of the Related Art

As an alternative to soldered, welded, cemented and precision-fitted connections, dental prosthetic components can be connected by casting-on. If a metallic connection with a closed joint is required for this, the joint component which is to be cast-on to (hereinafter designated the "primary part") and the joint component (hereinafter designated the "secondary part") which is to be cast-on, consist of an alloy which is made up of pure precious metals. As a rule high-carat, copper-free platinum- and iridium-containing gold alloys are used (cF. Lindigkeit in: G. K. Siebert: Dentallegierungen in der zahnärztlichen Prosthetik [Dental alloys in dental prosthetics], 1989, p880). If oxidizing alloys, e.g. a cobalt- or nickel-based alloy, are used, then provided the joint elements possess sufficiently retentive form, a tight connection is created initially. Due to the separating effect of the oxide layers on the joint elements, however, this latter exhibits an open metal joint apart from a few welded fusion points. This latter is soon attacked by crevice corrosion in the mouth and is enlarged. In the course of time the originally tightly-fitting elements can develop a distinctly visible and palpable loose fit which destroys the precision fit of the prosthesis.

Numerous dental objectives cannot be fulfilled by a single-casting process. As opposed to soldering or welding, the casting-on process avoids the additional problems associated with the transfer of sources of error involved in the production of a model for positioning and supporting the segments to be soldered; this results in a saving in both time and costs. The metallic cast-on connection using oxidising dental non-precious alloys is not considered possible in the-current state of the art.

SUMMARY OF THE INVENTION

It is, therefore, an objective of the invention to make available a dental prosthetic casting-on process which avoids the occurrence of a disruptive oxide or inactivating layer of oxide-forming alloys (base metals) under casting-on conditions.

This objective is fulfilled in the present invention by a dental prosthetic casting-on process in which a metal secondary part is cast-on to a metal primary part where the primary part used consists of an oxide-forming metal alloy whose casting-on surface is alloyed, prior to casting, with a reducing metalloid. Boron, silicon or phosphorus are the preferred reducing metalloids used. Such a metalloid is made to diffuse into the surface lattice of the primary element prior to casting. This process is advantageously enhanced with the aid of a halogenide, e.g. lithium fluoride, LiF. For the metalloids, boron or silicon can be used in the elementary form. The metalloid can, however, also be used in the form of a reactive compound.

The objective is further realized by means of a primary part which is characterized therein that it comprises an oxide-forming dental alloy (base metal) which in its surface casting-on zone exhibits a boron and/or silicon and/or phosphorus content.

The following advantages can be achieved by implementation the invention:

It is possible to produce a metallic cast-on joint between a primary part made of a base-metal alloy and secondary element made of a base-metal alloy.

It is, however, also possible to produce a metallic cast-on joint between a base-metal alloy primary part and a precious metal secondary part.

Pre-treatment of the base-metal alloy primary part prior to the casting-on of the base-metal alloy secondary part and the casting-on process itself can be performed in any dental laboratory.

Pre-treatment of the primary part prior to casting-on can, however, also be per formed on a mass production basis on the premises of the primary part manufacturer.

Further advantages of the invention can be deduced from the following description, illustrations and claims.

A primary part can, for example, take the form of a root canal post. In another embodiment the primary part can exist in thee form of a dental prosthetic accessory part, suitable for bilateral casting-on with oxide-forming dental casting alloys; this accessory part consists of a plate with at least one peripherally protruding anchorage arm for fixation within the investment mass.

The solution to the stated objective, as proposed in the invention, is very versatile, as a result of which numerous different applications are feasible. Amongst these are various ready-made attachments such as sliding, jointed and bar attachments, press-stud and movement-regulating mechanisms and other dental components such as a root canal post or a bridge framework.

BRIEF DESCRIPTION OF THE DRAWINGS

FIGS. 1 and 2 illustrate components made of a base-metal alloy which can be cast-on to.

FIGS. 3a and 3b show a root canal post for casting-on to in accordance with the invention.

DETAILED DESCRIPTION OF THE PREFERRED EMBODIMENTS

Figure 1:
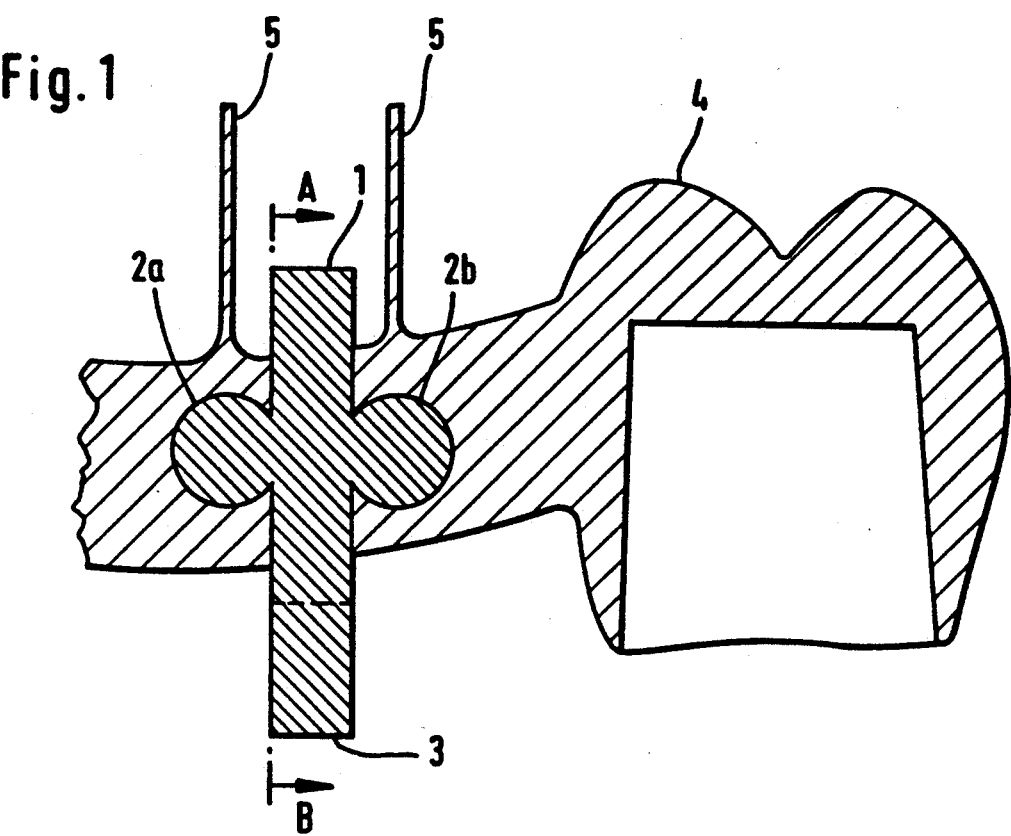

Cobalt-, nickel-, iron-, chromium- or niobium-based alloys are mainly used as base-metal alloys. Some metalloids are suitable as reducing media; these can be made to diffuse, in part reversibly, into the surface lattice structure of the alloy and, at a casting-on temperature of between 1100° and 1500° C. (depending on the alloy), to develop an adequate reduction effect in situ. This guarantees defect-free metallic fusion between the primary and secondary parts by means of casting-on. Consequently the advantages of the casting-on technique in accordance with the proposed process are available also for oxide-forming dental alloys, particularly if base-metal alloys are used.

In accordance with the invention, therefore, a base-metal alloy secondary part may be cast on a base-metal alloy primary part without difficulty. If desired, however, a secondary part made from a conventional gold alloy can be cast-on to a primary part in accordance with the invention.

Many processes are known in the prior art whose objective is to produce a surface metalloid accumulation, particularly of boron, in a workpiece. The purpose of these known methods is to produce a hardened layer which penetrates as far as possible into the underlying material and thereby to improve its wear resistance and/or corrosion characteristics. The treatment times required to achieve this boron-enrichment effect vary between a number of hours and several days. By contrast, the objective of the process according to the invention is not to form such a layer, and the treatment period with the metalloid used is comparatively brief, of the order of one minute. Any surface layer formations produced by the process in accordance with the invention must still be completely removed, as explained below.

To prevent an unnecessary reaction with the furnace atmosphere towards the end of the pre-heating phase at temperatures between 900° and 950° C. and consequent premature exhaustion of the reducing capacity of the boron which has diffused into the lattice, a graphite-containing investment mass can be used and the metalloid-prepared surface of the primary part covered with a thin protective platinum foil. The use of a metalloid prepared retention device makes possible the spatial separation of the hollow-space systems intended for different alloys, within a common mould, which with successive casting produces a common composite object by means of bilateral casting-on at the retention device.

If, in a preferred embodiment of the invention, the element boron in metalloid form is allowed to diffuse into the surface of the primary part, even nickel-based alloys with an aluminium content of up to 2%, which are characterized by particularly resistant inactive and oxide layers, may be joined perfectly by means of casting-on.

Alternatively to elementary boron, boron carbide may be used; similarly, a reactive Zintl phase high in silicon content, e.g. of chromium or other transition metals, may be used instead of elementary silicon. The metalloid should be incorporated into the surface lattice solely in a physical sense, as a constituent of the alloy, without forming compounds similar in type to the Zintl phases in accordance with stoichiometric or other chemical laws or forming hard material. Such phases or substances would produce isolating layers or zones which would prevent the casting-on process.

With the process according to the invention, a halogenide may advantageously be utilized. One of these, such as lithium fluoride, forms with the metalloid a volatile and highly reactive metalloid-halogenide compound (e.g. boron fluoride or silica fluoride), of which it is assumed that under the conditions governing the process, presumably in accordance with some site-exchange mechanism, it can be made to diffuse into the metal surface. It seems, therefore, that in the process according to the invention the halogen serves as a vehicle. It is a particularly straightforward matter as a result of this halogen attack to induce the reactants employed to produce the desired reaction in accordance with the invention.

The reduction of the primary part surface is brought about by the respective use of the boron, silicon or phosphorus element itself, presumably in that these diffuse into the surface metal lattice of the primary part in the sense of a local micro-alloying process. Apart from the pure elements, such compounds as release boron, phosphorus or silicon can also be employed as a source for the three metalloids. The number and kind of such available compounds is incalculably great. The number of borides alone can barely be calculated so those skilled in the art can abstract from the appropriate tables suitable substances with less stable elementary crystalline structure which correspond to their special alloying requirements. The already-mentioned halogen supplement can, however, induce the desired reaction in such metalloid compounds which under other conditions are regarded as "refractory"; then, however, the reaction times can be considerably longer than quoted above.

Scouring of the primary part of residues and reaction products of the reactants after the reaction is necessary because only structure-bound metalloid is desirable at the theoretically ideal sole, individual lattice sites in the surface, for only the metalloid can react at the casting-on temperatures. Residues of the reactants on the primary part surface exert a harmful influence since they react with one another as a consequence of chain and aggregate formation of the metalloid atoms. They would, therefore, largely cease to be wettable as regards metals. In the process according to the invention, the metalloid compounds can solely be used as a source for the metalloid itself and therefore do not remain on the surface of the primary part at all.

Polished sections of structures cast-on in accordance with the invention indicate, in addition to a defect-free metallic jointing of the segments, that the reaction products, to the extent that they are soluble in the metal, are presumably incorporated as betides into the crystal structure and otherwise are displaced from the cast-on joint into the investment mass in the form of insoluble dross.

Figure 2:
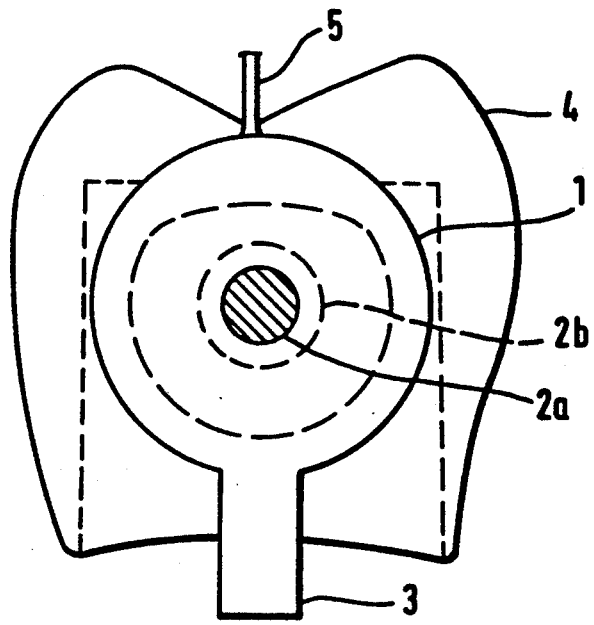

As shown in FIGS. 1 and 2, accessory parts made from base-metal alloys can be rendered capable of being cast-on to by means of the process according to the invention. The accessory part consists of a plate 1 of any desired form, but tending towards the circular, which at its centre bears bilaterally at least one retention device 2a, 2b and at the periphery at least one anchorage arm 3, illustrated here by means of an example in the shape of an arm. The diameter of the plate is greater than that of the retention devices. The accessory part is incorporated by bilateral casting-on as a construction element at the junction of the parts to be cast in different alloys within the same dental prosthesis, where traditionally soldering, welding or cementation would have be employed. With a telescopically anchored prosthesis, for example, the accessory part is incorporated into the connector between the external part of the telescope 4 and the wax model of the east framework in such a way that the anchorage arm and the periphery of the plate 1 remain free of wax, to be subsequently held by the investment mass. The retention devices 2a, 2b are completely and sufficiently thickly (min. 0.5 mm) covered by the modelling wax of both the framework and the connector 4. Both the skeleton and telescope models are provided with separate casting channels and sprues 5. Thereby there is created for each alloy a separate system of voids within the mould. The spatial separation is brought about by the incorporated accessory parts which connect the elements of the dental prosthesis made from different alloys by bilateral casting-on into a single uniform whole as a modified single-cast piece, without any special transfer or soldering process.

As shown in FIGS. 3a and 3b, a conventional dental prosthetic component in accordance with the invention made from an oxide-forming alloy, i.e. a root canal post, is rendered capable of being cast-on to provide a crown core build-up, in the absence of the natural tooth crown. Only the occlusal part adjacent to the component of the post 1 to be anchored in the dental root canal needs to be covered by a layer a capable of being cast-on to. The root canal-retained components can be separated from the coronal portion by a groove such that that part the post at the level of the groove becomes a connector d which leads to the coronal portion of the post e which is cast-on as a retainer of the whole root canal post in the form of a coronal core abutment for the replacement tooth (not shown). In addition to the coronal portion of the root canal-anchored segment of the post, the connector d and the retainer e comprise two layers through the application of an external layer capable of being cast-on to.

In the following, the process according to the invention is described through the example of rendering the surface of the primary part capable of being cast-on to by the application of boron. The process is analogously modified for the use of silicon or phosphorus, where it is expedient to use the latter in the form of a metallophosphide, e.g. copper or manganese phosphide. Boron enrichment is the preferred method, as thereby even base-metal alloys containing up to about 2% aluminium, can be rendered receptive for casting-on.

WORKING EXAMPLE

High-grade, commercial amorphous boron is mixed with an aqueous, saturated lithium fluoride solution to form a slurry with the consistency of oil paint and applied to excess with hair brush onto the casting-on surface of the primary part. After drying in a technical vacuum of a rotary pump (residual pressure up to a maximum of 20 mbar is harmless), said primary part, thus prepared, is heated for 1 minute to an approximate temperature of between 900° and 950° C. A dental ceramic furnace or also a glass flask, capable of being inductively heated by microwave energy, can be used for this following cooling, boron residues as well as all traces of dross are removed down to the metallic surface by blasting with corundum powder of 25 μm grain size at a blasting pressure of 3 bar.

It is of decisive importance that no traces of the reaction crust remain, as these produce an isolation effect during casting-on and prevent metallic union. In addition, the primary part surface is cleansed in an ultrasonic bath (aqua dest., 70° C.) for 3 min and subsequently degreased with steam under pressure before being covered with a thin layer of platinum. This is produced, for example, by thermic decomposition of an unstable platinum salt or by electrolytic immersion. A layer thickness of a few hundred rim, roughly estimated by interference colours or barely perceptible mirror imaging, is adequate.

We claim:

1. A dental prosthetic joining process comprising the steps of:
   a) furnishing a primary part made of an oxide-forming metal alloy;
   b) alloying a casting-on surface of the primary part with a reducing metalloid by causing the reducing metalloid, selected from the group consisting of boron, silicon, and phosphorus, to diffuse into a surface lattice of the primary part with aid from lithium fluoride, LiF;
   c) furnishing a secondary part made of metal;
   d) casting the second part on the casting-on surface of the primary part;
   whereby a dental prosthetic comprising a metallic cast-on connection of a primary and secondary part is provided; and
   wherein the primary part consists essentially of an oxidizing dental non-precious alloy.

2. A dental prosthetic joining process according to claim 1, wherein step b) comprises the steps of:
   b1) providing the reducing metalloid from the group consisting of borides, silicides, and phosphides;
   b2) forming an aqueous solution of said metalloid;
   b3) adding the lithium fluoride in a solution to said aqueous solution;
   b4) applying the mixture of the lithium fluoride solution and said aqueous solution onto a clean surface of the primary part in areas of the casting-on surface,
   b5) heating the thus prepared primary part at a temperature of 600°–1000° C.

3. A process as claimed in claim 1, wherein one of boron and silicon is used in its respective elementary form as said metalloid.

4. A process as claimed in claims 1 or 2, wherein the metalloid is used in the form of a reactive compound.

5. A process as claimed in claim 4, wherein one of a boride, silicide, and phosphide in the form of an aqueous slurry is used as the reactive compound.

6. A process as claimed in claim 1, further comprising the steps of:
   cooling the primary part;
   scouring the primary part clean of residues and reaction products of reactants; and
   covering the cleansed surface with a platinum precipitate.

* * * * *